US006673987B1

(12) United States Patent
King

(10) Patent No.: US 6,673,987 B1
(45) Date of Patent: Jan. 6, 2004

(54) STRATEGY FOR MAINTAINING PREGNANCY

(75) Inventor: Timothy J. King, Midlothian (GB)

(73) Assignee: Geron Corporation, Menlo Park, CA (US)

( * ) Notice: Subject to any disclaimer, the term of this patent is extended or adjusted under 35 U.S.C. 154(b) by 0 days.

(21) Appl. No.: 09/538,867

(22) Filed: Mar. 29, 2000

(30) Foreign Application Priority Data

Mar. 24, 2000 (GB) .............................. 0007297

(51) Int. Cl.$^7$ ........................ G01N 33/00; C12P 21/00; A01K 67/00; A01K 67/027; C12N 15/00
(52) U.S. Cl. ................................ 800/21; 800/3; 800/8; 800/4; 800/14
(58) Field of Search ............................ 800/14, 3, 4, 8, 800/21

(56) References Cited

U.S. PATENT DOCUMENTS

| | | | |
|---|---|---|---|
| 5,366,888 A | 11/1994 | Fry et al. ............... | 435/240.21 |
| 5,496,720 A | 3/1996 | Susko-Parrish et al. .. | 435/240.2 |
| 5,573,933 A | * 11/1996 | Seamark et al. .......... | 435/172.3 |
| 5,843,754 A | 12/1998 | Susko-Parrish et al. ...... | 435/240 |
| 5,905,042 A | 5/1999 | Stice et al. ................. | 435/373 |
| 5,922,854 A | * 7/1999 | Kumar et al. .............. | 536/23.5 |
| 5,942,435 A | 8/1999 | Wheeler ..................... | 435/325 |
| 5,994,619 A | 11/1999 | Stice et al. ................. | 800/21 |
| 6,077,710 A | 6/2000 | Susko-Parrish et al. ...... | 435/375 |
| 6,147,276 A | 11/2000 | Campbell et al. ............. | 800/24 |
| 6,252,133 B1 | 6/2001 | Campbell et al. ............. | 800/24 |
| 6,436,701 B1 | 8/2002 | Evans et al. ................. | 435/325 |

FOREIGN PATENT DOCUMENTS

| | | |
|---|---|---|
| WO | WO 97/07668 | 3/1997 |
| WO | WO 97/07669 | 3/1997 |
| WO | WO 98/27214 | 6/1998 |
| WO | WO 98/57538 | 12/1998 |
| WO | WO 99/01164 | 1/1999 |
| WO | WO 00/22098 A | 4/2000 |

OTHER PUBLICATIONS

Onishi et.al.; Pig Cloning by Microinjection of Fetal Fibroblast Nuclei, 2000, Science, vol.289: 1188–1190.*
Moreadith et.al.; Gene targeting in embryonic cells: the new physiology and metabolism, 1996, J. Moi. Med. 75: 208–216.*
Seamark; Progress and Emerging Problems in Livestock Transgenesis: a Suimmary Perspective, 1994, Reprod. Fertil. 6: 653–657.*
RK Christenson et al.,Journal of Animal Science, "Maintenance of Unilateral Pregnancy in the Pig with induced *Corpora Lutea*," Feb. 1971, vol. 32, No. 2, pp. 282–286.*
LW Johnson et al., Theriogenology, "Optimization of Embryo Transfer Protocols for Mice," 1996, 46;1267–1276.*

EL Feussner et al., Teratology, "A Decade of Rabbit Fertility Data: Study of Historical Control Animals," 1992, 46:349–365.*
Merriam–Webster's Collegiate Dictionary 10th Ed., p. 847 (1998).*
Blum–Reckow, B., et al., "Transfer of Porcine Embryos After 3 Days Of In Vitro Culture", *J. Anim Sci*, 69(8):3335–42(1991).
Cameron, RD., et al., "Practical Experience with Commercial Embryo Transfer in Pigs", *Aust Vet J.*, 66(10):314–8(1989).
Christenson, RK., et al., "Maintenance of Unilateral Pregnancy in the Pig with Induced *Corpora Lutea*", *J. Anim Sci.*, 32(2):282–286.
Duziuk, P., "Reproduction in the Pig", *Reprod. In Domestic Anim., Academic Press, Inc.*, 4:471–489 (1991).
Ellicott, A.R., et al., "Maintenance of Pregnancy in Prepuberal Gilts", *J. of Anim Sci.*, 37(4):971–973 (1973).
Ellicott, A.R., et al., "Minimum Daily Dose of Progesterone and Plasma Concentration for Maintenance of Pregnancy in Ovariectomized Gilts", *Bio of Reprod.*, 9:300–304(1973).
Geisert, R.D., et al., "Embryonic Steroids and the Establishment of Pregnancy in Pigs", *J. Reprod. Fert., Suppl.*, 40:293–305 (1990).
Gordon, I., "The Sow's Oestrous Cycle and Associated Events", *Controlled Reproduction in Pigs*, 3:60–76 (1997).
Han, YM., et al., Growth Retardation of Inner Cell Mass Cells in Polyspemic Porcine Embryos Produced in Vitro, *Bio of Reprod.*, 60:1110–1113(1999).
Han, YM., et al., "Pronuclear Location Before the First Cell Division Determines Ploidy of Polyspemic Pig Embryos", *Bio. Of Reprod.*, 61:1340–1346 (1999).
Jeyasingham, MD., et al., "*Escherichi Coli* K88 Receptor Expression in Intestine of Disease–Susceptible Weaned Pigs", *Vet Microbiol*, 68(3–4):219–34 (1999).
Joliff, W., et al., "Parthenogenic Development of In Vitro–Matured, In Vivo–Cultured Porcine Oocytes beyond Blastocyst", *Bio. Of Reprod.*, 56:544–548 (1997).

(List continued on next page.)

Primary Examiner—Deborah Crouch
Assistant Examiner—Joseph Woitach
(74) Attorney, Agent, or Firm—J. Michael Schiff; David J. Earp

(57) ABSTRACT

Pregnancy in animals such as the pig usually does not continue to term when there are only a few embryos in the uterus. Currently available technology for maintaining pregnancy involves a series of hormone injections, and the failure rate is high. It has now been discovered that pregnancy can be maintained by complementing fertile embryos in the uterus with additional embryos that aren't expected to survive the full term of the pregnancy. Particularly suitable are parthenogenetic embryos, formed by activating and diploidizing unfertilized oocytes. The carrier embryos are engrafted into the uterus of a surrogate female, and the pregnancy continues to term without further intervention— even if the number of fertile embryos are below the minimum litter size. This provides valuable biological material that can be used for transplantation, the production of pharmaceuticals, and for agricultural use.

22 Claims, No Drawings

OTHER PUBLICATIONS

Kikuchi, K., et al., "Developmental Competenc, After Transfer to Recipients, Of Porcine Oocytes Matured, Fertilized, and Cultured In Vitro", *Biol Reprod.*, 60(2):336–40 (1999).

Liu, L., et al., "Factors Affecting Electrical Activation of Porcine Oocyte Matured In Vitro", *Anim. Reprod. Sci.*, 48:67–80 (1997).

Loi, P., et al., Development of Parthenogenetic and Cloned Ovine Embryos: Effect of Activation Protocols, *Bio. Of Reprod.*, 58:1177–1187 (1998).

Polge, C., et al., "Time of Cessation of intrauterine Migration of Pig Embyros", *J Amer. Sci.* 31:565–566(1970).

Spies, H.G.,et al., "Maintenance of Early Pregnancy in Ovariectomized Gilts Treated with Gonadal Hormones"; *J. Anim. Sci.* 19:114–118.

Wang, W.HI., et al., "Effects of Oocyte Maturation Media on Development of Pig Embryos Produced by In Vitro Fertilization", *J. of Reprod. And Fert.*, 111:101–108 (1997).

Blum–Reckow, B., et al., "Transfer of Porcine Embryos After 3 Days of In Vitro Culture", *J. Anim. Sci*, 69:3335–3342 (1991).

Li, J., et al., "Technical Note: Porcine Non–Surgical Embryo Transfer", *J. Anim. Sci*, 74:2263–2268 (1996).

Wallenhorst, S., et al., "Transfer of Pig Embryos to Different Uterine Sites", *J. Anim. Sci*, 77: 2327–2329 (1999).

Nagy et al., Derivation of completely cell culture–derived mice from early–passage embryonic stem cells, Proc. Natl. Acad. Sci. USA 90:8424 (1993).

Bethauser, et al., Production of cloned pigs from in vitro systems, Nat Biotechn 18:1055 (2000).

Bondioli, et al., Cloned pigs generatied from cultured skin fibroblasts derived from a H–transferase transgenic boar, Mol Reprod Dev 60:189 (2001).

Dai, et al., Targeted disruption of the a1,3–galactosyltransferase gene in cloned pigs, Nat Biotechn 20:251 (2002).

Denning, et al., Deletion of the a(1,3)galactosyl transferase (GGTA1) gene and the prion protein (PrP) gene in sheep, Nat. Biotechnol. 19:559 (2001).

De Sousa, et al., Evaluation of Gestational Deficiencies in Cloned Sheep Fetuses and Placentae, Biol. Repro. 65:23 (2000).

De Sousa, et al., Somatic Cell Nuclear Transfer in the Pig: Control of Pronuclear Formation and Integration with Improved Methods for Activation and Maintenance of Pregnancy, Biol. Repro. 66:642 (2002).

Diamond, et al., A human CD46 transgenic pig model system for the study of discordant xenotransplantation, Transplantation 71:132 (2001).

Dinnyes, et al., Somatic Cell Nuclear Transfer: Recent Progress and Challenges, Cloning and Stem Cells 4:81 (2002).

Hammer, et al., Production of transgenic rabbits, sheep and pigs by microinjection, Nature 315:680 (1985).

Hawley, Genetic modification of pigs by nuclear transfer, Xenotransplantation 9:159 (2002).

King, et al., Embryo Development and Establishment of Pregnancy After Embryo Transfer in Pigs: Coping with Limitations in the Availability of Viable Embryos, Repro. 123:507 (2002).

Lai, et al., Production of a–1,3–Galactosyltransferase Knockout Pigs by Nuclear Transfer Cloning, Science 295:1089 (2002).

Lai, et al., Transgenic pig expressing the enhanced green pluorescent protein produced by nuclear transfer using colchicine–treated fibroblasts as donor cells, Mol Reprod Dev 62:300 (2002).

McCreath, et al., Production of gene=targeted sheep by nuclear transfr from cultured somatic cells, Nature 405:1066 (2000).

Notarianni, et al., Derivation of pluripotent, embryonic cell lines from the pig and sheep, J Reprod Fert Suppl 43:255 (1991).

Paleyanda, et al., Transgenic pigs produce functional human factor VIII in milk, Nat. Biotechnol. 15:971 (1997).

Uchida, et al., Production of transgenic nimiature pigs by pronuclear microinjection, Transgenic Res 10:577.

Wheeler, Development and validation of swine embryonic stem cells: a review, Reprod Fertil Dev 6:563 (1994).

Zhu, et al., Improvement of an Electrical Activation Protocol for Porcine Oocytes, Biol. Repro. 66:635 (2002).

* cited by examiner

STRATEGY FOR MAINTAINING PREGNANCY

RELATED APPLICATIONS

This application claims priority under 35 USC §119(a) to an application with the same title filed in the UK Patent Office on Mar. 24, 2000.

TECHNICAL FIELD

This invention relates generally to the field of embryo transfer. More particularly, it relates to factors that allow pregnancy to reach term following artificial engraftment of a fertile embryo in animal species such as ungulates.

BACKGROUND

There are now a variety of powerful techniques for developing new artificial strains of animals. These strains hold considerable promise for producing biological material for use in human and veterinary medicine, research, and agriculture.

Many of these techniques involve embryo transfer, in which a fertile embryo is engrafted into the uterus of a surrogate host. Pregnancy is a complex physiological transformation involving a number of signaling events, some of which emanate from the embryos in utero. In some species, a plurality of embryos must be present in order for pregnancy to be maintained. If less than the critical number of embryos is present, the corpora lutea regress and the embryos are not carried to term. When artificial embryo transfer is employed to initiate pregnancy in these species, it is often too difficult or too costly to transfer enough embryos for the pregnancy to be viable.

The estrous cycle of the sow is reviewed in the following publications: I. Gordon, pp. 60–76 in "Controlled Reproduction in Pigs" Vol. 3, CAB International, 1997; P. Dziuk et al., pp. 471–489 in "Reproduction in Domestic Animals", $4^{th}$ ed. P. T. Cupps, Academic Press Inc., 1991; R. D. Geisert et al., J. Reprod. Fert., Suppl. 40:293–305, 1990; and W. W. Thatcher et al., J. Animal Sci. 62 (suppl. 2):25–46, 1986.

Pigs normally deliver a litter of about 11 piglets. Following fertilization, a dialogue between endometrial epithelium and trophectoderm of the developing conceptus is important for pregnancy to be maintained. The normal reproductive cycle lasts 21 days, and unless specific signals are received the uterus secretes prostaglandin into the circulation 15 days after ovulation. This causes the corpora lutea (formed from follicles after they have ovulated) to regress, allowing the development of another group of follicles that grow to a pre-ovulatory size by day 21. The follicles release estrogen, which causes a surge in luteonizing hormone, triggering ovulation and starting the whole cycle over again.

If the eggs released by the follicles are successfully fertilized, they migrate around the uterus of the pig, and by 10–11 days are evenly spaced throughout the tract. The growing embryos provide signals that act locally or systemically. One such signal (thought to be mediated by estrogen) redirects secretion of prostaglandin from uterine cells to within the lumen of the uterus. This prevents regression of the corpora lutea, which in turn maintains raised levels of progesterone, preventing resumption of the estrus cycle and allowing the pregnancy to continue.

If there are not embryos occupying about 50% of the uterus before day 10 of the cycle, then the corpora lutea regresses and the estrus cycle is resumed. The critical number of embryos for maintaining pregnancy in the pig is about 3–4. However, if all the embryos are removed from one of the two horns after day 15, pregnancy is still successfully maintained to term (Dziuk et al., supra).

Current methods for artificially maintaining pregnancy typically rely on administering hormones that mimic the signals released by embryos or artificially maintain progesterone levels, preventing resumption of the estrous cycle.

Spies et al. (J. Anim. Sci. 19:114, 1960) conducted studies to determine the hormonal requirements for maintaining pregnancy in swine. Subcutaneous injections of progesterone and estrone were started 72 hours after breeding with a fertile bore. The percentages of embryo survival and the numbers of live embryos per pregnant gilt were significantly less for the treated animals than for the untreated controls.

Ellicott et al. (Biol. Reprod. 9:300, 1973a) conducted studies to measure the minimum quantity of estrogen and progesterone necessary to maintain pregnancy. Gilts were bred artificially or naturally on the first day of estrus, and ovariectomized under halothane anesthesia. Hormone was administered by inserting silicone capsules in the abdominal cavity. Pregnancy was maintained at a progesterone dose as low as 28.6 mg/day, and there was no added benefit of including 5 μg estradiol. No ovarian estrogen was necessary after day 10. A concentration of 4 ng/mL of progesterone in peripheral plasma appeared to be the minimum to maintain pregnancy.

Ellicott et al. (J. Animal Sci. 37:971, 1973b) studied the effects of various hormone combinations on the induction of an accessory set of corpora lutea for maintaining pregnancy. A significantly higher proportion of inseminated gilts were pregnant at day 30 when treated with estrogen-progestogen combinations. Oral administration of 200 μg melengestrol acetate and 1 mg estradiol on day 12 resulted in pregnancy in 4 out of 10 inseminated gilts. Five gilts pregnant at day 60 were removed from treatment, and two of these farrowed 5–6 piglets to term.

Christenson et al. (J. Animal Sci. 32:282, 1971) studied the maintenance of unilateral pregnancy in the pig with induced corpora lutea. The gilts were injected with pregnant mare serum and human chorionic gonadotrophin prior to the $11^{th}$ day of pregnancy to induce a second set of corpora lutea. This increased the percentage of gilts with a nonpregnant uterine horn that maintained pregnancy to 25–37 days of gestation.

U.S. Pat. No. 5,366,888 reports enhanced maintenance of pregnancy using leukemia inhibitory factor (LIF) in embryo culturing. Following introduction into foster mothers of embryos cultured in vitro in the presence of LIF, the maintenance of pregnancy is enhanced relative to that seen following introduction of embryos that had not been cultured with LIF. Embryos cultured in a medium optimally containing 1000–5000 units/mL of LIF is proposed to help maintain pregnancy in sheep.

In practice, administering hormones to a surrogate mother has a sub-optimal success rate in maintaining pregnancy in animals that have received an embryo transfer. In the laboratory where the present invention was made, the best treatment regime involving hormones alone was found to maintain pregnancy in only 26% of treated pigs. Embryos were also transferred into pigs that have already been mated. In these experiments, 37% of the pigs carried the transferred embryos. However, ultrasound at day 35 is unable to distinguish the transferred embryos from the embryos resulting from insemination—so it was not possible to determine which of the females were carrying the high value transferred embryos.

In view of the limitations of currently available technology, there is a pressing need to develop new artificial methods to maintain pregnancy.

SUMMARY OF THE INVENTION

This invention provides a technique for maintaining pregnancy in a female to which a fertile embryo has been transferred. The technique involves placing additional infertile embryos into the uterus, which have the effect of generating signals that allow the pregnancy to continue. The additional embryos typically maintain pregnancy through the early critical period, and then are reabsorbed or otherwise eliminated before the end of term. This allows viability of the engrafted fertile embryos to be monitored later in pregnancy, and helps avoid overcrowding of the uterus.

Embodiments of this invention include methods for maintaining pregnancy in a female pregnant with one or more fertile embryos, by engrafting into the uterus of the female one or more infertile embryos, thereby allowing the pregnancy to reach term, or at least until the fertile embryo is at a stage that it is viable ex utero. Also embodied in the invention are pregnant animals and birthed animals that result from the application of such methods.

The female is treated according to the invention generally because she is at risk of not carrying the fertile embryo to term due to potential lack of a signal that is usually required to maintain pregnancy. This can be caused, for example, because a signal produced by the embryo for maintaining pregnancy is missing or defective, because there is a problem in signal transduction, or because there is an insufficient number of embryos to provide adequate signal. In certain species, the viability of the pregnancy depends on the number of embryos in the uterus, such as an ungulate like the domestic swine.

The fertile embryo can be present in the uterus of the pregnant animal as a result of mating or embryo transfer. The infertile embryos can be engrafted simultaneously with the fertile embryo, or at an earlier or later time, typically early enough during the pregnancy to prevent regression of the corpora lutea. Depending on the period of pregnancy for the species being treated, the infertile embryos continue to develop in utero until at least about the 15$^{th}$ day of gestation. They are typically eliminated before the pregnancy reaches term, which may help prevent overcrowding. Progress of fertile and infertile embryos can be monitored if desired by diagnostic techniques such as ultrasound.

Exemplary infertile embryos are parthenogenetic embryos made, for example, by diploidizing and activating an oocyte of the same species as the female. Other infertile embryos suitable for use in this invention are cells with abnormal ploidy, such as polyspermic embryos. Sometimes, at least five, ten, twenty, or even more infertile embryos are engrafted into the uterus so that a high enough number will last through the critical period.

In particular embodiments of this invention, at least one of the fertile embryos has grown from a cell produced by transfer of a cell nucleus obtained from a first individual to an oocyte of a second individual with a different genotype from that of the first. The fertile embryos can be grown from a cell produced by transfer of a cell nucleus containing DNA that has been genetically altered into an oocyte. In some embodiments, chromosomal DNA in the embryonic cell has been genetically altered to express a heterologous gene, and/or altered to prevent expression of a gene that would otherwise be expressed.

Particular embodiments of this invention are methods for maintaining pregnancy in a pig, comprising engrafting the pig with one or more fertile embryos containing chromosomal DNA that has been genetically altered, plus one or more parthenogenetic embryos, whereby the number of fertile embryos and parthenogenetic embryos is sufficient to prevent regression of the corpora lutea, thereby allowing the pregnancy to reach term. Also embodied is a pig pregnant with one or more fertile embryos containing chromosomal DNA that has been genetically altered, plus one or more parthenogenetic embryos.

Further embodiments of this invention are methods for producing a mammal with chromosomal DNA that has been genetically altered by artificially engrafting into the uterus of a female a fertile embryo containing nuclear DNA that has been genetically altered, so that the female becomes pregnant with the embryo; artificially engrafting into the uterus of the female one or more infertile embryo(s) before, after or at the same time as the fertile embryo; and then birthing a mammal from said female that results from intrauterine development of the fertile embryo. Also embodied is a mammal having chromosomal DNA that has been genetically altered, produced according to a method of this invention.

Yet another embodiment of this invention is a method for producing a protein (optionally a human protein), which involves maintaining pregnancy in a female according to a method of this invention, wherein a fertile embryo in the female comprises an expressible gene encoding the protein; harvesting biological material from the birthed animal or its progeny (either solid tissue or a biological fluid, such as milk); and using the material to purify the protein. Another embodiment of the invention is a method for producing tissue suitable for transplantation (for example, into a human), which involves maintaining pregnancy in a female, wherein the chromosomal DNA of a fertile embryo has been genetically altered to inactivate a gene that encodes an antigen or encodes a protein that creates an antigen that is xenogeneic to the transplant recipient (such as Galα(1,3) Gal); and harvesting tissue from the birthed animal or its progeny. Also embodied in the invention are proteins, biological material, and tissues obtained according to such methods.

These and other embodiments of the invention will be apparent from the description that follows.

DETAILED DESCRIPTION

It has been discovered that pregnancy can be maintained by complementing fertile embryos in the uterus with additional embryos that usually do not survive the full term of the pregnancy. Using this technique, valuable embryos can be reliably developed in utero, in litters that are below the usual minimum size for the species being used.

Particularly suitable as infertile carrier embryos are parthenogenetic embryos, formed from an oocyte without fertilization by a male. For example, matured pig oocytes are activated using electrical pulses, and then diploidized using cytochalasin B. The carrier embryos are then placed in the uterus of a synchronized female along with the fertile embryo, and the pregnancy continues to term without the necessity for further intervention. This provides biological tissue that can be used for a number of valuable purposes, including agriculture and veterinary use, transplantation, and the production of pharmaceuticals on a commercial scale.

Definitions

The term "embryo" as it is used in this disclosure refers to an organism developing in the uterus of a species of interest at any time after fertilization or intrauterine transfer, not limited to a particular developmental period.

A "fertile embryo" is an embryo with a diploid genotype that is capable of producing a viable neonate of the respective animal species.

An "infertile embryo" or "carrier embryo" is an embryo that is typically incapable of surviving the full term of pregnancy without intervention. Exemplary is a parthenogenetic embryo, usually (but not necessarily) of diploid genotype, produced from a female gamete without any genetic contribution from a male gamete. Other types of embryos that can meet this definition comprise cells that are haploid, triploid, tetraploid, or have any other abnormal ploidy. This includes embryos that are mosaic of different ploidy, such as a mosaic of diploid and tetraploid cells.

An "embryonic cell" is either a single cell or a particular member of a group of cells, wherein either the single cell or the group of cells as a whole is capable of developing into an embryo in utero. The term includes but is not limited to a fertilized oocyte, a chimeric cell created by transfer of a nucleus from a donor cell into an enucleated oocyte or other embryonic cell, a particular cell present in a developing embryo, or a particular cell present in a mass of cells cultured in vitro for engraftment in utero.

The terms "engrafting" or "transplanting", in reference to embryo manipulation, refer to any process known in the art for artificially introducing one or more embryos into the uterus (including the uterine horns) of a female animal. The engrafted embryo or blastocyst can be fertile or infertile; it may or may not become implanted to the endometrium, and may or may not give rise to a viable neonate.

A cell is said to be "genetically altered" when genetic material such as a polynucleotide has been introduced into it. The definition also includes the progeny of a cell so altered that has inherited the introduced polynucleotide, or a copy thereof. The polynucleotide may contain a sequence that is exogenous to the cell, it may contain native sequences in an artificial arrangement (e.g., an encoding region linked to a different promoter), or it may provide additional copies of a native encoding sequence. The polynucleotide can be introduced by transfection using electroporation or liposome-mediated transfer, homologous recombination, transduction using a viral vector, any combination thereof, or any other technique known in the art. The polynucleotide will often comprise a transcribable sequence encoding a protein of interest, which enables the cell to express the protein at an elevated level. In the context of the present application, a "genetically altered cell" has a genetic alteration that is inheritable by progeny of the cell. For example, an embryo having genetically altered DNA, if carried to term, will give rise to a neonate that has cells containing the genetic alteration.

"Biological material" refers to any material obtained from a biological organism. Biological material obtained from a mammal can include biological fluids, such as milk, plasma, serum, lymph, saliva, and urine. It can also include solid material, such as cells in a particular organ, and fluid extracts of such material.

An "expressible gene" is a nucleotide sequence in chromosomal DNA operatively liked to transcription control elements that permit it to be transcribed into RNA in a particular cell or organism. Genes that encode a protein sequence of interest are also typically linked to translation control elements, such that the RNA transcription can be translated inside the cell into the protein.

"Operatively linked" refers to relationship between genetic elements in which the function of one element influences the function of another element. For example, an expressible encoding sequence is operatively linked to control elements such as promoters and enhancers that permit transcription, and typically to control elements such as translation initiation sequences, stop codons, and signals for polyadenylation.

General Techniques

Unless otherwise noted, the practice of this invention can be carried out by employing standard techniques of genetic engineering, protein manipulation, and cell culture. Textbooks that describe standard laboratory techniques include "*Molecular Cloning: A Laboratory Manual*", 2nd Ed. (Sambrook et al., 1989); "*Oligonucleotide Synthesis*" (M. J. Gait, ed., 1984); "*Animal Cell Culture*" (R. I. Freshney, ed., 1987); the series "*Methods in Enzymology*" (Academic Press, Inc.); "*Gene Transfer Vectors for Mammalian Cells*" (J. M. Miller & M. P. Calos, eds., 1987); "*Current Protocols in Molecular Biology*" and "*Short Protocols in Molecular Biology, 3rd Edition*" (F. M. Ausubel et al., eds., 1987 & 1995); and "*Recombinant DNA Methodology II*" (R. Wu ed., Academic Press 1995).

Texts that describe reproductive techniques and embryo transfer in animals include "*Controlled Reproduction in Pigs*" Vol. 3 (I. Gordon, CAB International, 1997); "*Manual of the International Embryo Transfer Society: A procedural guide and general information for the use of embryo transfer technology emphasizing sanitary procedures*", $3^{rd}$ ed. (Stringfellow et al., Savoy, Ill.: International Embryo Transfer Society, Savoy Ill.); "*Embryo transfer in farm animals: A review of techniques and applications*" (K. J. Betteridge, ed., Agriculture Canada Monographs No. 16, Ottawa, 1977).

Production of Infertile Embryos

This invention provides for the maintenance of pregnancy in any species wherein the viability of pregnancy depends in part on one or more signals provided by the embryo—either a molecular signal, such as the secretion of a hormone, or a physical signal, such as a volume or mass change detectable by the pregnant female. The invention can be implemented, when the embryo(s) which it is desired to carry to term are believed to be inadequate in providing such signals.

In one illustration, an embryo is somehow defective in providing adequate signal that is usually provided by embryos of the species in question, perhaps because of a genetic abnormality or some other disturbance that interferes with generation of the signal, or transduction of the signal into the host. In another illustration, ongoing pregnancy requires signal to be provided by a plurality of embryos in the uterus, and maintenance of pregnancy is positively correlated with the number of embryos in the uterus. Where the number of fertile embryos present is less than what is usually required, then the probability of maintaining pregnancy can be enhanced by implementing the techniques of this invention. In general terms, the invention is applicable to all mammals without limitation. The strategy can be employed in human and veterinary medicine, and for research purposes. In particular embodiments, the invention is practiced on ungulates including but not limited to Artiodactyla, including ruminants and suids, which in turn are exemplified by Suidae, particularly the domestic swine. In another embodiment, the invention is practiced on rodents (including mice and rats) that also give birth to large litters, and generally require a minimum number of embryos to maintain pregnancy.

The technique involves engrafting a female with one or more infertile embryo(s) at a time when the female is pregnant with one or more fertile embryo(s) of about the same age, from which it is desired to produce viable neonates. The combination of fertile and infertile embryos provides a situation in which sufficient signals are provided to promote maintenance of the pregnancy, and maturation of a valuable embryo. Typically, the combined signals prevent regression of the corpora lutea, which would otherwise indicate termination of the pregnancy and resumption of the estrous cycle.

The infertile embryos are generally selected to remain viable at least through the critical period for maintaining the corpora lutea in the species of interest (about the $15^{th}$ day of pregnancy in the pig), but then to be reabsorbed or expelled before the pregnancy reaches term, which may help prevent overcrowding. In the pig, it is typically preferable for the infertile embryos to be reabsorbed, expelled, or otherwise eliminated by about the $30^{th}$ day, in order to avoid the risk of overcrowding of the uterus as the embryos grow. For many large animal agricultural species, the infertile embryos remain in the female for 10, 15, 20, or 25 days, selected at least to exceed the critical period, and are eliminated by the $5^{th}$, $4^{th}$, $3^{rd}$ or $2^{nd}$ month, in order of increasing preference. It will be recognized that species that have substantially shorter gestation periods will require scaling down of this time frame appropriately. More generally, the infertile embryos remain in the female for 5%, 10%, or 15% of the full term of pregnancy, but are eliminated before 80%, 60%, or 40% of term, as appropriate.

An exemplary type of infertile embryo is the parthenogenetic embryo. Mammalian oocytes can be parthenogenetically activated by a variety of physical and chemical stimuli, reviewed in D. C. Whittingham, pp. 205–231 of "Parthenogenesis in mammals", ed. C. A. Finn, Oxford Rev. Reprod. Biol. Vol. 2, Clarendon Press, Oxford, 1980. Any technique in the art for activating oocytes may be suitable, providing the oocytes are activated to divide without fertilization.

Effective physical stimuli include mechanical manipulation, thermal changes, or electrical stimulation. Effective chemical stimuli include osmotic or ionic changes (divalent cations or calcium ionophores), or enzymatic challenge (Wang et al., Biol. Reprod. 58:1357, 1998). U.S. Pat. No. 5,496,720 outlines a process for parthenogenetic activation of bovine oocytes by increasing intracellular levels of divalent cations, and reducing phosphorylation of cellular proteins, for example a serine-threonine kinase inhibitor. Protein synthesis inhibitors, such as puromycin and cyclohexamide can be effective (Siracusa et al., J. Embryol. Exp. Morphol. 43:157, 1978). Chemicals that stimulate the G protein/phospholipase C cascade ($IP_3$, GTP-G-S) have also successfully activated oocytes (Machaty et al., Biol. Reprod. 52:753, 1995; Busa et al., J. Cell Biol. 101:677, 1984). Oocytes can also be activated by electrical pulses. Factors affecting electrical activation in vitro are reported by Liu et al. (Anim. Reprod. Sci. 48:67, 1997).

Loi et al. (Biol. Reprod. 58:1177, 1998) compare different activation protocols and the subsequent rates of embryonic development in the sheep. Combinations of chemical activators induced pronuclear development at a slightly higher rate than physical activation. Ionomycin plus 6-dimethylaminopurine (6-DMAP) were used to produce parthenogenetic blastocysts that were transferred into previously synchronized ewes. Over 70% of the parthenogenotes were viable on day 21 of pregnancy, but dead by day 25.

Joliff et al. (Biol. Reprod. 56:544, 1997) report the development of parthenogenetically activated oocytes from the pig. Oocytes were matured in vitro, and then stimulated with an electric pulse at 36–48 hours. Electrically stimulated oocytes were transferred to the oviduct of a synchronous gilt and developed the to the filamentous stage (containing an intact embryonic disc, 10% development beyond the blastocyst stage) at 14 days after activation.

Parthenogenetic embryos for use in this invention can be produced using oocytes from whole ovaries. Follicular fluid is aspirated, and used as a source of cumulus-oocyte complexes. The complexes are typically matured for about 2 days in a suitable maturation medium, such as Waymoth's medium, typically supplemented with eCG and/or hCG and other factors that enhance maturation (Jolliff et al., supra). Also suitable are recently ovulated oocytes obtained from females by surgical or mechanical extraction of their oviducts (Loi et al., supra). Ovulated oocytes typically do not need to be matured in the same fashion as complexes extracted from ovaries. Oocytes prepared by either method are then activated and diploidized by appropriate methods.

An exemplary method for maturing oocytes in vivo is conducted as follows. Follicles about 3–8 mm in size are selected from ovaries of recently killed animals, and an oocyte complex is aspirated from a selected follicle. The oocyte complex is cultured for about 36–48 hours in a suitable medium, such as described by Wang et al. (J. Reprod. Fertil. 111:101, 1997). Oocytes matured in vitro are denuded of cumulus (either manually, or by treating with a suitable protease, such as 600 IU/mL hyluronidase). Oocytes matured under these conditions have improved competence for development into parthenogenetic embryos.

Oocytes can also be collected from live donors by surgical procedures or flushing the fallopian tubes with medium. The developmental competence can be improved by harvesting the oocytes about 42–50 hours after injecting gonadotropin in a sufficient dose to induce superovulation. Effective hormones with gonadotrophic activity include pregnant mares serum gonadotropin (PMSG), hCG, equine chorionic gonadotropin (eCG), and gonadotropin releasing hormone. Optionally, two separate administrations can be performed. For example, PMSG is injected first towards the end of the diurnal rhythm of the animal to recruit follicles to be ovulated, and hCG is injected ~88 hours later to induce ovulation and maturation of the oocyte. The mature oocyte is then harvested ~46 hours later to prepare infertile embryos for use in this invention. Further information on the maturation of oocytes both in vitro and in vivo can be obtained from International Patent Application PCT/GB99/03384.

An exemplary method for producing parthenogenetic embryos from domestic swine proceeds as follows: Oocytes are optimally matured in vitro or in vivo, according to the procedures just described. They are then activated electrically by an optimized protocol. For example, matured pig oocytes are activated by pulses of 5 sec×5 Volts AC, 3×80 $\mu$sec pulses of 1 kiloVolts/cm (20 Volts/200 $\mu$m) DC in 0.3 M mannitol, 50 $\mu$M $CaCl_2$, 100 $\mu$M $MgCl_2$. The activated oocytes are then diploidized by culturing in 7.5 $\mu$g/mL cytochalasin B in NCSU23 medium for 6–8 h at 38.5° C., 5% $CO_2$ in air. The oocytes are then cultured overnight in NCSU23 until transfer the next day.

In a variation of this method, cyclohexamide is added to the medium to a concentration of 10 $\mu$g/mL, and the period of treatment after activation is reduced to 4 hours. After pulsing in mannitol buffer as before, the activated oocytes are diploidized by culturing in NCSU medium containing both 7.5 $\mu$g/mL cytochalasin B and 10 $\mu$g/mL cyclohexamide in NCSU23 medium at 38.5° C., 5% $CO_2$ in air, for only 4 hours. The oocytes are then cultured overnight in NCSU23 until transfer the next day.

Other types of infertile embryos are also suitable for use in this invention. Included are embryos that have a euploid genotype and have somehow been adapted so that the usual course is for it to be expelled or absorbed before the end of term. For example, an embryo may be genetically altered to not survive beyond a certain number of cell divisions, or to render them susceptible to a toxic drug that could be administered in utero. Another type of infertile embryo are embryos that have abnormal ploidy, and which, as a consequence, are unlikely to survive the full length of pregnancy. This includes embryos comprising cells that are haploid, triploid, or tetraploid, including mosaics. Such embryos can be obtained from poly-pronuclear eggs. See Han et al. (Biol. Reprod. 60:1110, 1999a) and Han et al. (Biol. Reprod. 61:1340, 1999b) regarding polyspermic pig embryos produced in vitro. Briefly, oocytes are matured if necessary, and fertilized in vitro. About 10 h after fertilization, the eggs were centrifuged at ~12,000×g for ~10 min, and then classified individually as to whether they are two-pronuclear (2PN) or poly-pronuclear (PPN, 3 pronuclei or more). About 53% of 2PN and 40% of PPN develop to the blastocyst stage in vitro. PPN eggs are more likely to produce fetuses that are not strictly diploid, and therefore less likely to survive the full term of pregnancy.

Suitable infertile embryos are typically maintained in culture until required for engrafting into the surrogate female.

Use of Infertile Embryos to Maintain Pregnancy

Infertile embryos are typically engrafted in a female also engrafted with a fertile embryo, in order to increase the number of embryos in the uterus and thereby improve the probability that the fertile embryo will reach term and produce a neonate.

Fertile embryo of many different origins can be used for engrafting into the female host. Included are fertilized embryos obtained from females or inseminated as part of an in vitro fertilization technique. Using the technology of this invention, embryos from superior matings can be prepared in advance and stored frozen, then raised to term in low-numbered litters whenever desired. Also contemplated is maintaining the pregnancy of one or more fertile embryos present in the uterus through other means. For example, the female may have been made pregnant through the natural process of insemination, optionally facilitated by sildenafil citrate, or other medication, device, or environmental condition that enhances the frequency of an efficacious fertilization event.

This invention is particularly useful for the maturation of embryos that are produced in vitro by artificial manipulation of embryonic cells. For example, U.S. Pat. Nos. 5,905,042 and 5,994,619 relate to production of chimeric bovine and porcine animals using cultured inner cell masses. Of interest are embryos produced by transfer of a donor nucleus of one individual to an oocyte of another individual. International Patent Application WO 97/07669 (Roslin Institute) describes quiescent cell populations for nuclear transfer. International Patent Application WO 97/07668 (Roslin Institute) describes inactivated oocytes as cytoplast recipients for nuclear transfer. WO 99/01164 (University of Massachusetts) relates to cloning pigs using donor nuclei from differentiated cells.

Donor nuclei are obtained from a suitable donor cell, such as an in vitro manipulated embryonic cell, or an adult cell in germ-line configuration. Nuclear transfer is particularly effective if the nucleus of the donor cell is quiescent, which can be achieved by culturing the donor cell in a serum-free medium (WO 97/07669). In an exemplary method, the nucleus of a donor cell is transferred into an oocyte that is arrested in the metaphase of the second meiotic division, and subsequently activating the reconstituted cell. Briefly, unfertilized metaphase II oocytes are collected as follows: Female animals are synchronized using progestagen sponges for ~14 days, and induced to superovulate with single injections of follicle-stimulating hormone on two successive days. Ovulation is induced with a suitable dose of gonadotrophin-releasing hormone or an analog thereof (e.g., ~8 mg GnRH Receptal™, Hoechst, UK) on the following day. The oocytes are recovered by flushing from the oviduct one day later, washed, and enucleated by treating with cytochalasin B and aspirating the nucleus using a glass pipette. Enucleated oocytes are then placed into contact with a single cell which acts as the nucleus donor.

Fusion of the donor nucleus into the enucleated recipient cell is effected by placing the couplet in a fusion chamber and aligning it between the electrodes. Electrical pulses are then applied to induce fusion, typically a low-voltage AC pulse for several seconds, followed by a plurality of very short high-voltage DC pulses. Following an incubation period, activation is induced by application of an additional electrical pulse. The reconstructed zygote is then cultured for a time before engrafting into a surrogate female. Further details and alternative procedures are described in the patent publications cited above.

In certain embodiments of the invention, the chromosomal DNA is genetically altered to express a transgene, such as a heterologous gene construct. The transgene can be inserted into the genome of the nuclear donor cell by any suitable method in the art, including (but not limited to) homologous recombination and transduction using a virus that integrates into the genome as part of its replicative cycle. U.S. Pat. No. 5,591,625 relates to the preparation stem cells capable of augmented expression of certain gene products, signal transduction molecules, and cell surface proteins for therapeutic applications. U.S. Pat. Nos. 5,573,933 and 5,942,435 report methods for preparing transgenic pigs. International Patent Application WO 97/25413 reports the use of primordial germ cells from porcine or bovine embryos for obtaining chimeric ungulates that produce pharmaceutical products.

In some of these embodiments the transgene is an expressible gene comprising a nucleotide sequence that encodes a human protein that can be recovered from a tissue sample or bodily fluid, exemplified by but not limited to plasma and milk. Optimally, the encoding region will be operatively linked to control elements that specifically permit biosynthesis and secretion of the encoded protein into the bodily fluid. Suitable are control elements for other proteins naturally secreted into milk, such as lactoferrin, casein, and whey acidic protein. U.S. Pat. No. 5,565,362 provides DNA constructs with a casein promoter and a casein enhancer region. The protein product includes a signal peptide that is functional in mammary secretory cells to facilitate translocation of the protein across the Golgi membrane and secretion of the peptide into the milk. U.S. Pat. No. 5,700,671 claims methods for making transgenic animals producing oligosaccharides or glycoproteins in the milk, wherein the transgene comprises an encoding region for a heterologous glycosyltransferase. U.S. Pat. No. 5,880,327 claims transgenic mammals that produce milk containing human Factor VIII protein.

To obtain animals producing the desired human protein, a fertile embryo containing the transgene is then engrafted into a female in estrus. For production of protein from milk, the fertile embryo is optionally preselected to be an XX genotype; alternatively, female neonates are selected after birth. The pregnancy is maintained by engrafting one or more infertile embryos, and the fertile embryo matures and is birthed from the surrogate mother. After the neonate has grown to sufficient age, the tissue or body fluid containing the protein of interest is harvested. The protein can then be purified by a suitable combination of standard protein separation techniques, including but not limited to salt precipitation, ion exchange chromatography, gel exclusion chromatography, and affinity separation. Proteins that have therapeutic value can then be formulated into a medicament, in accordance with generally accepted procedures for the preparation of pharmaceutical preparations. See *Remington's Pharmaceutical Sciences* 18*th Edition* (1990), E. W. Martin ed., Mack Publishing Co., Pa.

In certain embodiments of the invention, the chromosomal DNA is genetically altered to prevent expression of a gene that would otherwise be expressed. For example, it is sometimes desirable to prevent expression of a histocompatibility marker or other antigen in an animal so that its tissues are transplantable to an allogeneic or xenogeneic recipient. Knock-out animals can be prepared by inactivating a gene of interest so that it is not expressed in the birthed animal. The gene can be inactivated by a number of different strategies, including altering or removing a control element (such as a promoter or a start signal for transcription or translation), or a critical part of the encoding sequence (such as the active site of an enzyme), or placing the encoding region out of phase, or by altering the specificity of the encoded protein. Any method in the art for accomplishing such disruption may be used, including but not limited to homologous recombination or directed point mutation.

In one illustration, animal tissue can be prepared without the Galα(1,3)Gal xenoantigen that causes hyperacute rejection when transplanted into human recipients. The Galα(1,3)Gal determinant is synthesized by a α(1,3) galactosyltransferase that places galactose onto a Galβ(1,4) GlcNAc (N-acetyl lactosamine) acceptor present on the surface of a number of different cell types, including endothelial cells that line the vasculature of transplant tissues. Targeting constructs are designed to delete or replace one or more of the six separate exons that typically make up the α(1,3)galactosyltransferase encoding region (Katayama et al., Glycoconj. J. 15:583, 1998). The constructs are used to genetically alter embryonic cells, and then cells are selected for successful targeting. To prevent formation of the Galα (1,3)Gal epitope in the adult animal, it is usually necessary for the animal to be homozygous for inactivated α(1,3) galactosyltransferase. This can be accomplished either by selecting for homozygous knock-outs in the embryonic cells, or by mating two animals that have inactivated α(1,3)galactosyltransferase in one haplotype. See U.S. Pat. Nos. 5,849,991 and 5,821,117. The genetically altered embryonic cell is then prepared for transfer in utero as a fertile embryo.

To improve the probability that the fertile embryo will reach term and produce a neonate in an individual in need of the techniques of this invention, the surrogate female is engrafted with one or more fertile embryos, and one or more infertile embryos. The total number of embryos is chosen so as to provide an adequate signal between both the fertile embryos and the infertile embryos for the pregnancy to be maintained. Typically, it is more convenient to introduce both the fertile embryos and the infertile embryos into the uterus at the same time. On some occasions, it may be desirable to engraft the fertile embryos before the infertile embryos, or vice versa. The number of infertile embryos used depends on the signal required for maintaining pregnancy in the animal species being employed.

Estrus in the surrogate female is typically synchronized artificially using a suitable combination of inducing agents. Cameron et al. (Aust. Vet. J. 66:314, 1989) discuss synchronization methods and other practical aspects for commercial embryo transfer in pigs. Blum-Reckow et al. (J. Anim. Sci. 69:3335, 1991) report experiments relating to transfer of pig embryos after long-term in vitro culture. Replacing medium every 12 h during culture improved survival, and pregnancy rate improved if the sexual cycle of recipients was 24 h behind that of the donor.

Fertile or infertile embryos can be introduced into the uterus of the recipient female using any suitable technique, including surgical methods. For example, U.S. Pat. No. 4,326,505 describes surgical procedures for embryo transplants in animals, in which the uterine horn is positioned in the peritoneal cavity proximate to the vaginal wall, a cannula is inserted through the vaginal wall and into the uterine horn, and the embryo is introduced through the cannula. Also included are non-surgical methods, using a suitable device to manipulate the injection port through the folds of the cervix to the bifurcation of the uterus. For example, devices and techniques for porcine non-surgical embryo transfer are reported by Li et al. (J. Anim. Sci. 74:2263, 1996). Wallenhorst et al. (J. Anim. Sci. 77:2327, 1999) describe the effect of transferring pig embryos to different uterine sites.

The number of infertile embryos that are engrafted will depend on several considerations. One consideration is the manner in which the pregnancy of the fertile embryo is at risk. In species where pregnancies of a single embryo can be carried to term, but the signal for maintaining pregnancy is somehow missing from the fertile embryo, then it may be sufficient to engraft just a single infertile embryo to overcome the deficiency. Another consideration is the number of embryos typically required to maintain pregnancy in the species, which can be predicted based on the typical smallest observed litter size. In this case, the number of infertile embryos should be chosen so that the total number of embryos exceeds the minimum number. Another consideration is the nature of the infertile embryos, and the probability that they will survive through the critical period and prevent regression of the corpora lutea. The number of embryos should be adjusted to compensate for the embryos that will be lost by the end of the period. A countervailing consideration is the risk that the uterus will become overcrowded when embryos are more developed. This caps the number of infertile embryos that should be engrafted. Where the infertile embryos are not expected to last until the point where overcrowding becomes a problem, then there is more latitude for engrafting a larger number. Even where pregnancy can be maintained by a single embryo, additional infertile embryos can be engrafted to improve the probability that the valuable fertile embryo will reach term.

By way of illustration, parthenogenetic embryos generated from pig oocytes have about a 40% to 60% chance of surviving to day 7 in culture, and probably even less of surviving past day 15. To implement this invention in a female pig, at least about 3–5 infertile embryos are typically engrafted where the purpose is to support pregnancy when just a single fertile embryo, since the minimum litter size is about 4 neonates. Accommodating the expected loss before the end of the critical period, the number of infertile embryos engrafted will frequently be at least 10. Since parthenogenetic embryos generally do not survive to the point where overcrowding becomes an issue, it is acceptable to engraft an even larger number of infertile embryos to improve the probability of success. Thus, it may be suitable to engraft 20, 40, 60, or even more infertile embryos to maintain the pregnancy. An alternative strategy is to improve the probability that parthenogenetic embryos will survive the critical period. In one approach, activated oocytes are grown in culture for 7 days, and those still surviving are then be engrafted into the uterus in support of the fertile embryo, which may or may not have been cultured in vitro for a similar period.

Once the fertile and infertile embryos have been engrafted, the pregnancy is then allowed to continue to term, or at least until at least one valuable fetus is viable outside the womb. It is permissible to treat the surrogate female during the pregnancy to further improve the chances that the pregnancy will reach term: for example, with hormone injections. However, such intervention is generally not required.

The following example is provided as a further guide to the practitioner, and is not intended to limit the invention in any way.

EXAMPLE

The experiment outlined in this section was undertaken to determine the viability of diploid parthenogenetic pig embryos at day 21, compared with normal fertilized embryos—either after embryo transfer, or by fertilization in situ. The capacity of parthenogenetic embryos to signal pregnancy in recipient gilts would be compared with fertilized embryos.

On Day 0 (the day of heat), some gilts were served by a male boar. Other gilts in heat were selected to receive a fertilized embryo or a parthenogenetic embryo.

Eggs recovered from a slaughter house were matured for 2 days. On Day 1, they were made into parthenogenetic embryos in the following manner. First, the eggs were denuded of cumulus (manually, or using a solution of 600 IU hyluronidase/mL). They were then activated electrically at 5 sec×5 Volts AC, 3×80 $\mu$sec pulses of 1 kiloVolts/cm (20 Volts/200 $\mu$m) DC in a buffer containing 0.3 M mannitol, 50 $\mu$M $CaCl_2$, and 100 $\mu$M $MgCl_2$. The activated eggs were diploidized by culture in 7.5 $\mu$g/mL cytochalasin B in NCSU23 medium for 6–8 h at 38.5° C., 5% $CO_2$ in air. The eggs were then cultured overnight in NCSU23 until transfer the next day.

On Day 2, fertilized embryos were surgically recovered from some of the gilts that had been inseminated on Day 0. Other mated groups were retained as the control group. In the second and third groups respectively, 20 fertilized embryos or 60 parthenogenetic embryos were transferred artificially into the uterus of gilts that displayed heat on Day 0.

On about Day 21, the animals were sacrificed and the uterine tract was examined for the number and size of surviving embryos. Results are shown in the following Table:

TABLE 1

Parthenogenetic Pig Embryo Viability

| Gilt | Day of Recovery | No. of Embryos | % of those Transferred | Mean Weight (g) | Mean crown rump length (mm) |
|---|---|---|---|---|---|
| CONTROL PIGS PREGNANT WITH FERTILIZED EMBRYOS | | | | | |
| 5383 | 21 | 8 | (not transferred) | 144.3 | 12 |
| 5561 | 20 | 19 | " | 80.5 | 8.8 |
| 5639 | 21 | 17 | " | 154.9 | 10.9 |
| PIGS PREGNANT WITH FERTILIZED TRANSFERRED EMBRYOS | | | | | |
| 4787 | 21 | 16 | 76% | 80.1 | 9.7 |
| 5606 | 21 | 19 | 95% | 204.1 | 11.7 |
| 4059 | 21 | 0 | 0 | — | — |
| PIGS PREGNANT WITH PARTHENOGENETIC TRANSFERRED EMBRYOS | | | | | |
| 5491 | 21 | 10 | 16% | 53.3 | 8 |
| 5374 | 21 | 0 | 0 | — | — |
| 5948 | 21 | 1 | 2% | 37.8 | 5 |
| 5732 | 20 | 0 | 0 | — | — |
| 5405 | 21 | 5 | 9% | 73.6 | 8.3 |

These results show that parthenogenetic pig embryos activated and diploidized in culture survive in utero to the 21 day point of gestation. The parthenogenetic embryos apparently provide the signals needed to maintain pregnancy for 21 days—which is beyond what is thought to be the critical time for maintaining pregnancy in swine.

What is claimed as the invention is:

1. A method for producing a non-human mammal in a species wherein maintenance of pregnancy depends on having a sufficient plurality of embryos in the uterus, comprising:
   a) combining at least one embryo produced by nuclear transfer with a plurality of infertile embryos of the same species produced by a method that does not involve nuclear transfer;
   b) engrafting the combined embryos into the uterus of a pseudo-pregnant female of the same species; and subsequently
   c) birthing a mammal from the female resulting from intrauterine development of the embryo produced by nuclear transfer.

2. The method of claim 1, wherein the infertile embryos are parthenogenetic embryos.

3. The method of claim 2, wherein the parthenogenetic embryos are produced by diploidizing and activating an oocyte of the same species as the female.

4. The method of claim 1, wherein the infertile embryos comprise cells with abnormal ploidy.

5. The method of claim 1, wherein at least five infertile embryos are engrafted into the uterus.

6. The method of claim 1, wherein the embryo produced by nuclear transfer contains chromosomal DNA that has been genetically altered.

7. The method of claim 6, wherein the chromosomal DNA has been genetically altered to express a heterologous gene.

8. The method of claim 6, wherein the chromosomal DNA has been genetically altered to prevent expression of a gene that would otherwise be expressed.

9. The method of claim 1, wherein the species is a domestic swine.

10. A method for producing a non-human mammal in a species wherein maintenance of pregnancy depends on having a sufficient plurality of embryos in the uterus, comprising:

a) engrafting at least one embryo produced by nuclear transfer into the uterus of a female of the same species;
b) engrafting into the uterus of the female a plurality of infertile embryos of the same species produced by a method that does not involve nuclear transfer at a time before or after a) so as to prevent regression of the corpora lutea and loss of the embryo produced by nuclear transfer; and subsequently
c) birthing a mammal from the female resulting from intrauterine development of the embryo produced by nuclear transfer.

11. The method of claim 10, Wherein the infertile embryos are parthenogenetic embryos.

12. The method of claim 11, wherein the parthenogenetic embryos are produced by diploidizing and activating an oocyte of the same species as the female.

13. The method of claim 10, wherein the infertile embryos comprise cells with abnormal ploidy.

14. The method of claim 10, wherein at least five infertile embryos are engrafted into the uterus.

15. The method of claim 10, wherein the embryo produced by nuclear transfer contains DNA that has been genetically altered.

16. The method of claim 15, wherein the chromosomal DNA has been genetically altered to express a heterologous gene.

17. The method of claim 15, wherein the chromosomal DNA has been genetically altered to prevent expression of a gene that would otherwise be expressed.

18. The method of claim 10, wherein the species is a domestic swine.

19. A method for maintaining pregnancy in a pig, comprising engrafting the pig with at least one fertile embryo plus one or more parthenogenetic embryos, whereby the number of fertile embryo(s) and parthenogenetic embryo(s) is sufficient to prevent regression of the corpora lutea, thereby allowing pregnancy to be maintained such that a mammal is produced from development of the fertile embryo in utero.

20. The method for maintaining pregnancy of claim 19, wherein the fertile embryo contains chromosomal DNA that has been genetically altered to include an expressible encoding region for a human protein, or to inactivate a gene that would otherwise be expressed.

21. A pig carrying at least one fertile embryo, plus one or more artificially engrafted embryos produced by parthenogenetic activation of an oocyte without nuclear transfer.

22. The pig of claim 21, wherein the fertile embryo contains chromosomal DNA that has been genetically altered to include an expressible encoding region for a human protein, or to inactivate a gene that would otherwise be expressed.

* * * * *